United States Patent
Lustenberger et al.

(10) Patent No.: US 10,508,110 B2
(45) Date of Patent: Dec. 17, 2019

(54) PROCESS FOR PREPARING 1-(4-METHANESULFONYL-2-TRIFLUOROMETHYL-BENZYL)-2-METHYL-1H-PYRROLO[2,3-B]PYRIDIN-3-YL-ACETIC ACID

(71) Applicants: Philipp Lustenberger, Basel (CH); Christian Mathes, Basel (CH); Zhongbo Fei, Changshu (CN); Bernard Riss, Basel (CH); Thierry Schlama, Basel (CH)

(72) Inventors: Philipp Lustenberger, Basel (CH); Christian Mathes, Basel (CH); Zhongbo Fei, Changshu (CN); Bernard Riss, Basel (CH); Thierry Schlama, Basel (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/763,562

(22) PCT Filed: Sep. 27, 2016

(86) PCT No.: PCT/IB2016/055777
§ 371 (c)(1),
(2) Date: Mar. 27, 2018

(87) PCT Pub. No.: WO2017/056001
PCT Pub. Date: Apr. 6, 2017

(65) Prior Publication Data
US 2018/0273530 A1    Sep. 27, 2018

(30) Foreign Application Priority Data

Sep. 29, 2015  (WO) ................ PCT/CN2015/091024

(51) Int. Cl.
*C07D 471/04* (2006.01)
*C07D 213/74* (2006.01)

(52) U.S. Cl.
CPC ......... *C07D 471/04* (2013.01); *C07D 213/74* (2013.01)

(58) Field of Classification Search
None
See application file for complete search history.

(56) References Cited

FOREIGN PATENT DOCUMENTS

WO    2005123731 A2    12/2005

OTHER PUBLICATIONS

De Gasparo, R. et al. Synlett vol. 26, pp. 197-200 2015.*
Raoul De Gasparo et al., "A Convenient Palladium-Catalyzed Azaindole Synthesis", Synlett, vol. 26, No. 2, pp. 197-200, Nov. 14, 2014.

* cited by examiner

*Primary Examiner* — Heidi Reese
(74) *Attorney, Agent, or Firm* — Daniel Woods

(57) ABSTRACT

This invention relates to novel processes for synthesizing [1-(4-Methanesulfonyl-2-trifluoromethyl-benzyl)-2-methyl-1H-pyrrolo[2,3-b]pyridin-3-yl]-acetic acid and to intermediates that are used in such processes.

20 Claims, No Drawings

PROCESS FOR PREPARING 1-(4-METHANESULFONYL-2-TRIFLUOROMETHYL-BENZYL)-2-METHYL-1H-PYRROLO [2,3-B]PYRIDIN-3-YL-ACETIC ACID

TECHNICAL FIELD

This invention relates to novel processes for synthesizing 1-(4-Methanesulfonyl-2-trifluoromethyl-benzyl)-2-methyl-1H-pyrrolo[2,3-b]pyridin-3-yl-acetic acid and to intermediates that are used in such processes.

BACKGROUND OF THE DISCLOSURE

The pharmaceutically active compound 1-(4-Methanesulfonyl-2-trifluoromethyl-benzyl)-2-methyl-1H-pyrrolo[2,3-b]pyridin-3-yl-acetic acid ("Compound A") is an antagonist of the G-protein coupled chemokine receptor homologous molecule expressed on Th2 lymphocytes ("CRTh2") that is useful for the treatment of several disorders such as asthma and atopic dermatitis. Compound A has the following chemical structure:

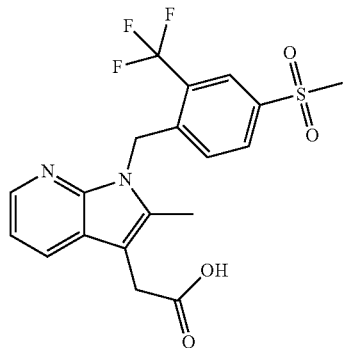

Compound A

[1-(4-Methanesulfonyl-2-trifluoromethyl-benzyl)-2-methyl-1H-pyrrolo[2,3-b]pyridin-3-yl]-acetic acid Compound A, methods of synthesizing Compound A and methods of treating various disorders using Compound A are referred to in U.S. Pat. No. 7,666,878 which issued on May 10, 2011, the contents of which are herein incorporated by reference in its entirety.

Although methods of producing Compound A are known, the present invention discloses for the first time a method of producing Compound A which has fewer steps, has a higher yield, and has a higher selectivity for Compound A. The invention accomplishes these features primarily via the use of a sigmatropic rearrangement which is described in more detail below. The advantages described above are exemplified in the examples that follow.

BRIEF SUMMARY OF THE DISCLOSURE

The invention relates to the compound having the formula:

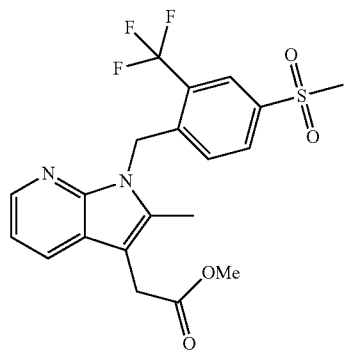

(C8)

Methyl 2-(1-{[4-methanesulfonyl-2-(trifluoromethyl)phenyl]methyl}-2-methyl-1H-pyrrolo[2,3-b]pyridin-3-yl)acetate This compound is an intermediate in the synthesis of Compound A.

This invention also relates to the compound having the formula:

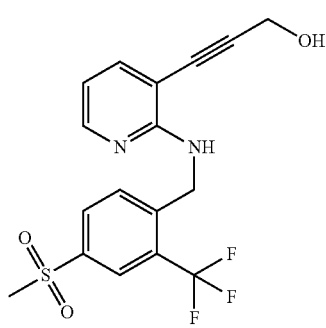

(C6)

3-[2-({[4-Methanesulfonyl-2-(trifluoromethyl)phenyl]methyl}amino)pyridin-3-yl]prop-2-yn-1-ol This compound is useful as an intermediate in the synthesis of both the compound of Formula C8 and Compound A.

This invention also relates to the compound having the formula:

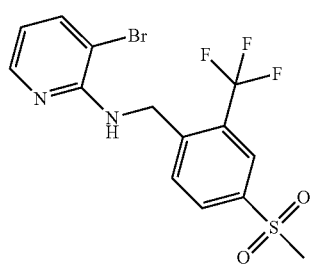

(C4)

3-Bromo-N-{[2-methanesulfonyl-4-(trifluoromethyl)phenyl]methyl}pyridin-2-amine This compound is useful in the synthesis of both compound C6 and Compound A.

This invention also relates to a process for preparing C4. The process comprises reacting a compound of the formula:

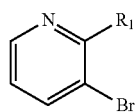
(C1)

Wherein R1 is selected from the group consisting of Br or NH₂ with a compound of the formula:

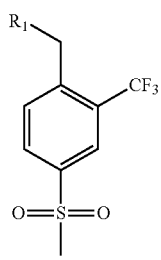
(C2)

Wherein R1 is selected from the group consisting of an aldehyde or amine, in the presence of an acid, preferably p-toluenesulfonic acid, trifluoroacetic acid, trichloroacetic acid or oxalic acid. When R1 of compound C1 is NH2 and R1 of C2 is an aldehyde, a compound of the following formula is formed:

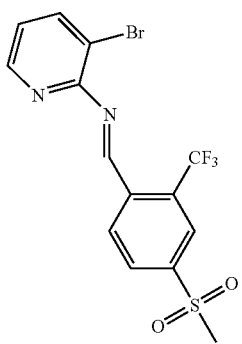
(C3)

3-Bromo-N-{[2-methanesulfonyl-4-(trifluoromethyl)phenyl]methylidene}pyridin-2-amine Compound C3 is then converted to compound C4 in the presence of a solvent, preferably a mixture of toluene with methanol, and sodium borohydride (NaBH₄). When R1 of compound C1 is Br and R1 of C2 is NH₂ no such conversion is necessary as compound C3 is not formed.

This invention also relates to a process for producing compound C6. The process comprises reacting a compound of the formula C4 with a compound of the following formula:

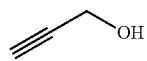
(C5)

in the presence of a catalyst, 1 or more solvents, a ligand, and a base. Preferred catalysts include palladium based catalysts such as palladium acetate and cupric catalysts such as cupric iodide, or palladium catalysts such as palladium on charcoal or palladium acetate, or palladium chloride. A preferred ligand is triphenylphosphine. Preferred solvents include ethanol, toluene, and isopropyl acetate. A preferred base include a tertiary amine like triethylamine or an inorganic base like potassium carbonate.

This invention also relates to a process for producing compound C8. The process comprises reacting compound C6 with a compound of the following formula:

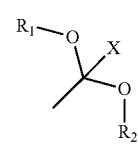
(C7)

wherein R1 and R2 are each independently a $C_1$-$C_6$ alkyl group which may be the same or different, and X is Y—Z, where Y is N, S, $SO_2$, or O and Z is H, O or a $C_1$-$C_6$ alkyl, in the presence of a catalytic amount of acid and a solvent. Organic acids such as acetic acid, propionic acid, or pivalic acid as well as Lewis acids montmorillonite, or immobilized acids, or acidic alumina are competent catalysts for the transformation. The solvent may be any solvent, however organic solvents such as methyl isobutyl ketone are preferred.

The resulting compound C8 is converted to Compound A via saponification in the presence of an acid and a base. Preferably, the acid is a strong acid such as hydrochloric acid. Preferred bases are strong bases such as sodium hydroxide. After saponification, Compound A is isolated and purified.

The sequence of steps outlined above can be integrated into an overall scheme for the production of Compound A. Such an integrated process is generally comprised of the following steps under suitable reaction conditions described herein:

(a) reacting compound C1 and C2 to form C4;
(b) reacting compound C4 with compound C5 to form C6;
(c) reacting compound C6 with compound C7 to form C8; and
(d) converting compound C8 to Compound A.

Also disclosed is a process for preparing C6 comprising (a) reacting a compound of the formula

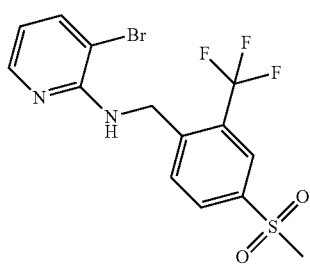
(C4)

with a compound of the formula

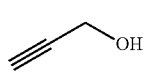 (C5)

in the presence of a catalyst, a reducing agent and 1 or more solvents. In one embodiment, the catalyst is palladium on charcoal. In another embodiment, the catalyst is palladium chloride. In yet another embodiment the catalyst is palladium acetate. In a further embodiment the catalyst is cupric iodide. Other embodiments utilize organic acids.

Appropriate solvents useful in the above process include ethanol, toluene, toluol, isopropyl acetate, and mixtures thereof. Any one of these solvents, or combinations thereof, can be used in conjunction with any of the catalysts above. For example, palladium on charcoal can be used in conjunction with ethanol, toluene, toluol, isopropyl acetate, and mixtures thereof. Similarly, palladium chloride can be utilized in conjunction with ethanol, toluene, toluol, isopropyl acetate, and mixtures thereof. Palladium acetate can also be used in conjunction with ethanol, toluene, toluol, isopropyl acetate, and mixtures thereof. As with the other catalysts, cupric oxide and organic acids can be used in conjunction with the solvents ethanol, toluene, toluol, isopropyl acetate, and mixtures thereof.

The invention also discloses the step of adding a strong acid to the mixture of C4, C5 and any of the catalysts described above (e.g., strong bases can be utilized with each of palladium on charcoal, palladium chloride, palladium acetate, cupric iodide and organic acids). The strong acid, such as pivalic acid can be in the presence of any solvent present as well. The solvents, as described above, can be any combination of ethanol, toluene, toluol, isoporopyl acetate, and mixtures thereof in combination with any catalyst as described above.

Alternatively, a strong base can be added to the mixture of C4, C6 the catalyst, the strong acid (if present) and any of the solvents (if present).

In yet another embodiment, a reducing agent such as NaBH4 or triphenylphsophine can be added to the mixtures of any combinations of solvents, bases, catalysts and acids.

The invention also comprises a process for preparing C8 comprising reacting a compound of the formula

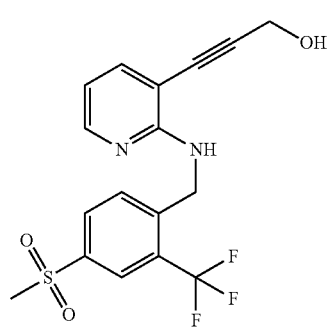 (C6)

with a compound of the formula

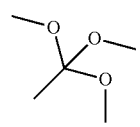 (C7)

in the presence of a catalyst and a solvent.

In some embodiments, the catalyst is an organic acid. In a preferred embodiment the catalyst is pivalic acid. In a preferred embodiment the solvent is methyl isobutyl ketone. In a particularly preferred embodiment the solvent methyl isobutyl ketone and the strong acid pivalic acid are utilized together.

The invention also relates to a process for preparing a compound of the formula

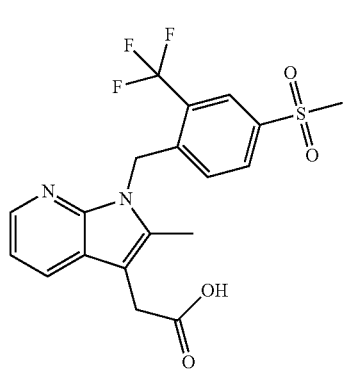 (Compound A)

[1-(4-Methanesulfonyl-2-trifluoromethyl-benzyl)-2-methyl-1H-pyrrolo[2,3-b]pyridin-3-yl]-acetic acid comprising:
(a) reacting a compound of the formula:

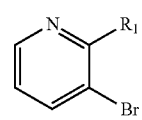 (C1)

wherein R1 is selected from the group consisting of Br or NH₂ with a compound of the formula:

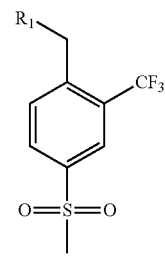 (C2)

wherein R1 is selected from the group consisting of an aldehyde or amine, in the presence of an acid, to form a compound of the formula

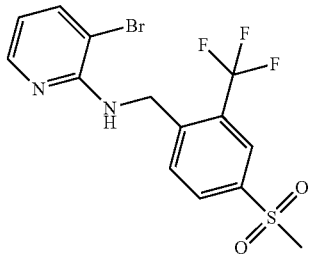
(C4)

(b) reacting the compound of formula C4 with a compound of the formula

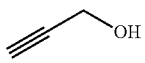
(C5)

in the presence of a catalyst, a reducing agent and 1 or more solvents to form a compound of the formula

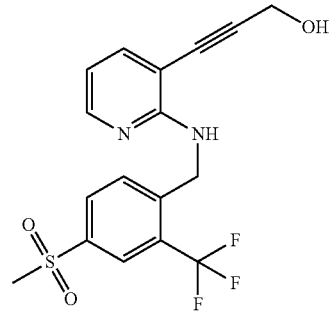
(C6)

(c) reacting the compound of formula C6 with a compound of the formula

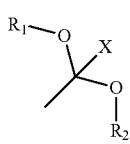
(C7)

wherein R1 and R2 are each independently a $C_1$-$C_6$ alkyl group which may be the same or different, and X is Y—Z, where Y is N, S, $SO_2$, or O and Z is H, O or a $C_1$-$C_6$ alkyl to form a compound of formula

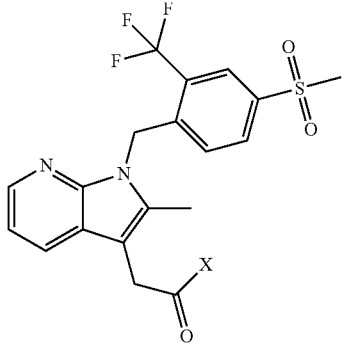
(C5)

or reacting a compound of formula C6 with a compound of the formula

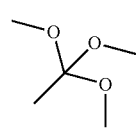
(C7)

in the presence of a catalyst and a solvent to form a compound of the formula

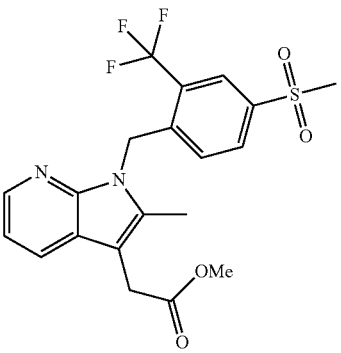
(C8)

(d) Converting the compound of formula C8 to Compound A by saponification of C8 in the presence of a strong base.

In one embodiment, the acid in step (a) above can be any of 1-p-toluenesoulfonic acid, trifluoroacetic acid, trichloroacetic acid and oxalic acid.

In yet another embodiment, the catalyst in step (b) can be any of palladium on charcoal, palladium chloride, palladium acetate, cupric iodide and organic catalysts. It should be understood by one of skill in the art that any of the acids stated above with regards to step (a) can be utilized with any of the catalysts described in this paragraph.

In yet another embodiment, the solvents in step (b) are any of ethanol, toluene, toluol, isopropyl acetate, and mixtures thereof. It is understood that any of the solvents described in this step can be used in any combination with any of the catalysts or acids listed in the preceding paragraphs.

Also disclosed is an embodiment wherein step (b) further comprises adding a strong acid to the mixture of C4, C5 and the catalyst. In yet another embodiment step (b) further comprises adding a strong base to the mixture of C4, C5 and the catalyst. It will be understood by one of skill in the art that the strong acid or the strong base can be used with any of the solvents, catalysts or other acids described in the preceding paragraphs.

In yet another embodiment the reducing agent in step (c) is triphenylphosphine. It will be understood by one of skill in the art that the reducing agent can be utilized with any previously enumerated catalyst, acid, or strong acid.

In a further embodiment the catalyst in step (c) is an organic acid such as pivalic acid. It will be understood by one of skill in the art that the reducing agent can be utilized with any previously enumerated catalyst, acid, or reducing agent.

DETAILED DESCRIPTION OF THE DISCLOSURE

In the discussion that follows, reference to compounds C1-C8 and Compound A are defined as they are defined above. The compounds and processes of this invention are depicted in the reaction scheme shown below:

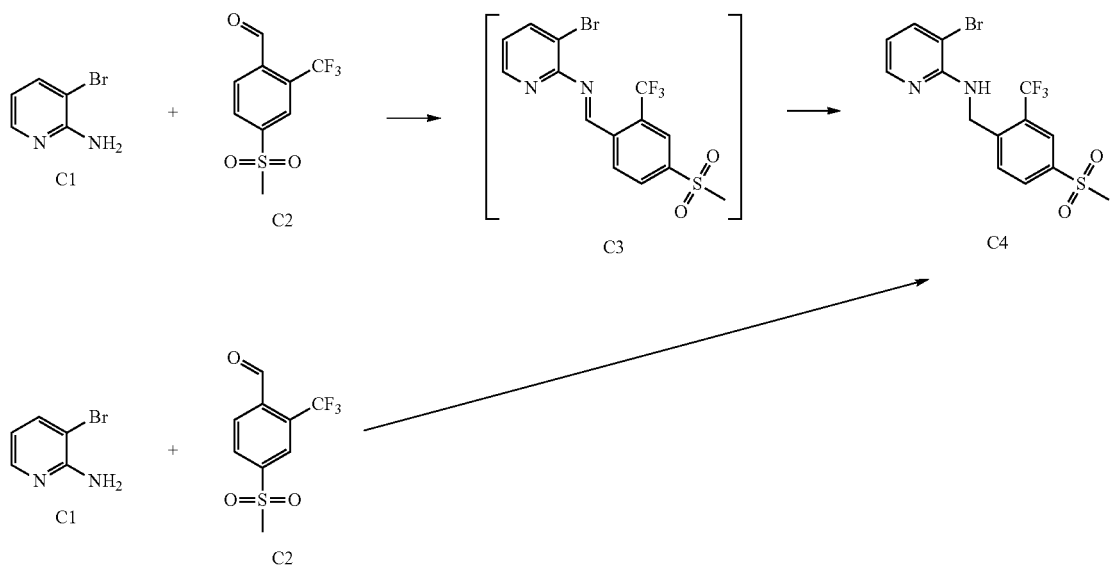

Reaction Scheme (Continued)

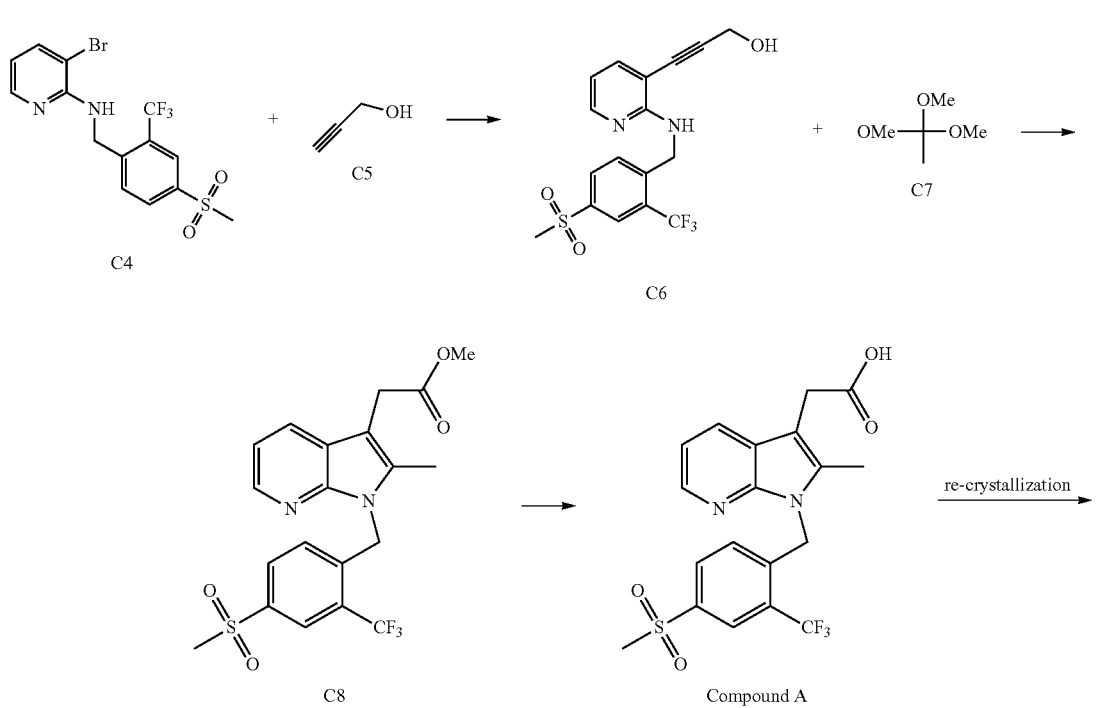

The current scheme of the invention advantageously increases yields and selectivity of Compound A by applying a rearrangement reaction to the free propargylic alcohol C6. This scheme enables the performance of the sigmatropic rearrangement of C6 to C8 under milder conditions and sets the system up for ring closure.

The process scheme starts with a condensation of amino pyridine C1 with aldehyde C2; removal of water leads to imine intermediate C3. The reaction proceeds in the presence of one or more solvents. The solvents can be any suitable solvent known in the art. Preferably the solvent is an organic solvent such as toluene. The reaction takes place in the presence of an acid catalyst, preferably p-tolusulfonic acid monohydrate. Other catalysts such as $H_3PO_4$, $H_2SO_4$, $SiO_2$, pyridinium p-Toluenesulfonate, $AlOxH^+$, where x is an integer from 0-4, trifluoroacetic acid, trichloroacetic acid, oxalic acid, tartaric acid, maleic acid, and fumaric acid may be used. Suitable reaction temperature conditions are from 100° C. to 140° C., with a range of 110° C. to 135° C. being preferred. Any water formed during the reaction is trapped and removed.

C3 is then reduced to compound C4. The conversion is achieved in the presence of a solvent and a reducing agent. Any solvent can be used, however preferred solvents are organic solvents, particularly preferred solvents are methanol, toluene, toluol, isopropyl ketone, and mixtures thereof. Suitable reducing agents include phosphine, triphenyl phosphine, $NaBH_4$, $LiAlH_4$ or other agents known in the art (e.g. silanes). Suitable reaction temperature conditions are from 40° C. to 60° C., with a range of 50° C. to 56° C. being preferred. Typical yields are greater than 90%, and purity of C4 is approximately 99%.

Alternatively, intermediate C4 is prepared by transition metal-catalyzed cross-coupling (amination) of 2,3-dibromo-pyridine C1 with benzyl amine C2 as shown in the Scheme above in the presence of a catalyst (e.g. palladium acetylacetonate), base (e.g. potassium carbonate) and a ligand (e.g. BINAP) in an high boiling solvent like anisole giving 46% C4 of high purity (>98%). Suitable reaction temperature conditions are from 110° C. to 180° C., with a range of 150° C. to 160° C. being preferred.

Sonogashira coupling of C4 with propargyl alcohol C5 to produce propynyl derivative C6 is achieved under a wide range of conditions using a catalyst, ligand, base, and solvents. Preferred catalysts include any palladium source like palladium on charcoal (Pd/C catalyst), or palladium salts like palladium acetate or palladium chloride, and any copper source as a second catalysts such as copper iodide (CuI) or copper chloride (CuCl). And preferred base include a tertiary amine such as triethylamine or an inorganic base such as potassium carbonate. Preferred ligands include triphenylphosphine. Suitable solvents include ethanol, isopropanol, tert-butanol, ethyl acetate, isopropyl acetate, butyl acetate, cyclopentylmethyl ether, tetrahydrofuran, dimethylformamide, toluene, xylene, cumol, and combinations thereof. The reaction work-up is carried out in the presence of strong acids and strong bases. Preferred examples include hydrochloric acid, ammonium hydroxide and sodium hydroxide. Suitable reaction temperature conditions are from 70 to 110° C., with a range of 75 to 85° C. being preferred. Typical yields are in the range of 75% and up; purity is typically greater than 98%.

In the most important step, C6 is treated with C7 in the presence of catalytic amounts of a weak acid like acetic acid, propionic acid, pivalic acid, acetic anhydride, montmorillonite, immobilized acids, or acidic alumina to provide methyl ester C8 via rearrangement reaction in the presence of one or more solvents. Suitable solvents include organic solvents; the preferred solvent is methyl isobutyl ketone. Preferred catalysts include acetic acid and pivalic acid. Suitable reaction temperature conditions are from 120° C. to 180° C., with a range of 140° C. to 150° C. being preferred. Typical yields are in the range of 75% and up; purity is typically greater than 99%. Alternatively, elevated temperatures of up to 300° C. can be used in the presence of suitable pressurizable equipment such as flow reactors and the like. In addition, if triethyl ortho-acetate is used instead of C7, then an ethyl ester analogue of Compound A is formed (not shown).

C8 is then converted to Compound A via saponification in the presence of a strong acid and a strong base. The preferred acid is hydrochloric acid and the preferred base is sodium hydroxide. Suitable reaction temperature conditions are from 40° C. to 80° C., with a range of 50° C. to 55° C. being preferred. Typical yields are in the range of 75% and up; purity is typically greater than 99%. To obtain the desired polymorphic or crystalline forms, Compound A is recrystallized in accordance with techniques well known in the art.

EXPERIMENTAL EXAMPLES

The following experimental examples illustrate the processes of the present invention and are not intended to limit the scope of the present invention as defined in the claims below.

Example 1a

Preparation of C4 (3-Bromo-N-{[4-methanesulfonyl-2-(trifluoromethyl)phenyl]-methyl}pyridin-2-amine)

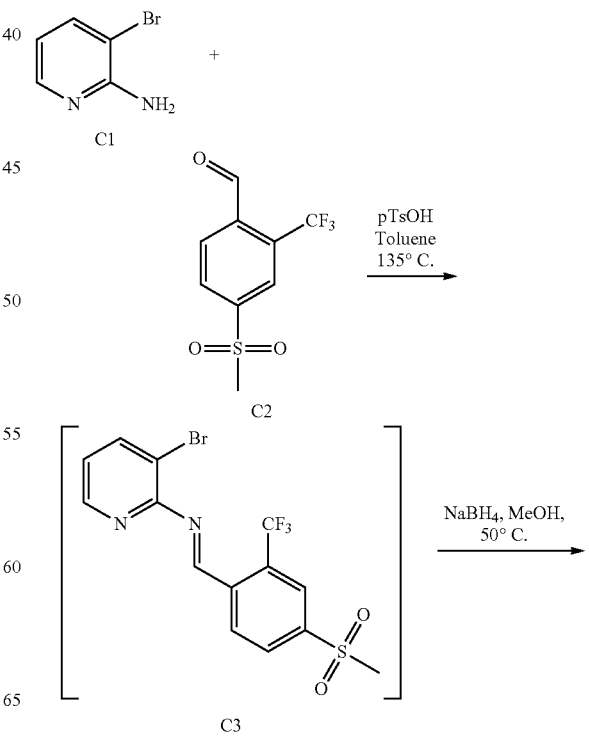

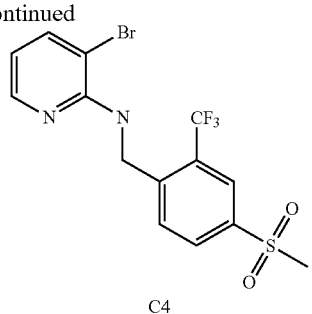

C4

36.5 g (210 mmol) of C1 (2-Amino-3-bromopyridine) and 50.5 g (200 mmol) C2 (4-Methanesulfonyl-2-(trifluoromethyl)benzaldehyde) were refluxed in 500 ml toluene under acid catalysis with p-toluenesulfonic acid monohydrate (0.78 g, 4 mmol) at a temperature of 145° C. in a Dean-Stark apparatus. The formed water is trapped; after a minimum of 15 hours the reaction was completed. The hot solution was cooled down to an internal temperature ("IT") of 50° C. and 40 ml of methanol was added. Sodium borohydride was added in 4 portions (8 g, 200 mmol) within 2 hours. Furthermore, the suspension was heated for 5 hours. During this time hydrogen gas was formed. Next, 100 ml water was added within 10 minutes and the pH was controlled by adding a mixture of 100 ml water and 14 g of acetic acid to adjust the pH to approximately 6. The reaction mixture was stirred for an additional hour. The phases were then separated and the toluene phase was washed with 200 ml of water. The toluene phase was then filtered; 450 g of toluene was distilled off under reduced vacuum. To the resulting solution 150 ml isopropanol was added while heating the solution to 85° C. The solution was cooled down to IT=0-5° C. within 2 hours and at IT 50° C. seed crystals were added. The resulting suspension was filtered. The residue was washed 2 times with 60 ml cold isopropyl ketone/heptanes (1:1 by volume) to form C4 (3-Bromo-N-{[4-methanesulfonyl-2-(trifluoromethyl)phenyl]methyl}pyridin-2-amine). The wet C4 was dried in the oven at a temperature of 50° C. for 12 hours. 77.1 g (94.2%) of white substance was isolated. Calculated yield was 94.2%. Purity was greater than 99%.

Example 1b

Preparation of C4

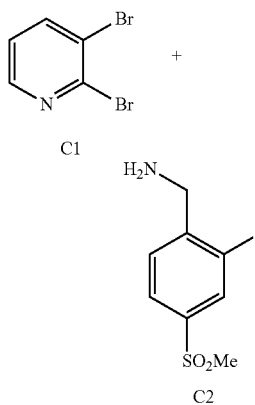

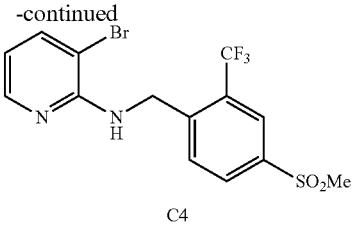

C4

In a 100 mL round-bottomed flask (t=g) 2,3-dibromopyridine (1 g, 4.221 mmol), (4-(methylsulfonyl)-2-(trifluoromethyl)phenyl)methanamine (1.3 g, 5,133 mmol), and $K_2CO_3$ (1.8 g, 13.024 mmol) were suspended in Anisole (20 mL) to give a brown suspension. BINAP (0.5 g, 0.803 mmol) and PALLADIUM(II) ACETYLACETONATE (0.2 g, 0.891 mmol) were added. The reaction mixture was heated to 155° C. for 3 h. LCMS at t=3 h (m+1=408/410) showed the reaction was complete. The reaction mixture was filtered, precipitate washed with DCM. The reaction mixture was concentrated and the crude product was added to a silica gel (100 g) column and was eluted with EtOAc/Heptane (0%-70%). Isolated yield of C4 was 0.79 g (46%).

Example 2

Preparation of C6(3-[2-({[4-Methanesulfonyl-2-(trifluoromethyl)phenyl]-methyl}amino)pyridin-3-yl]prop-2-yn-1-ol)

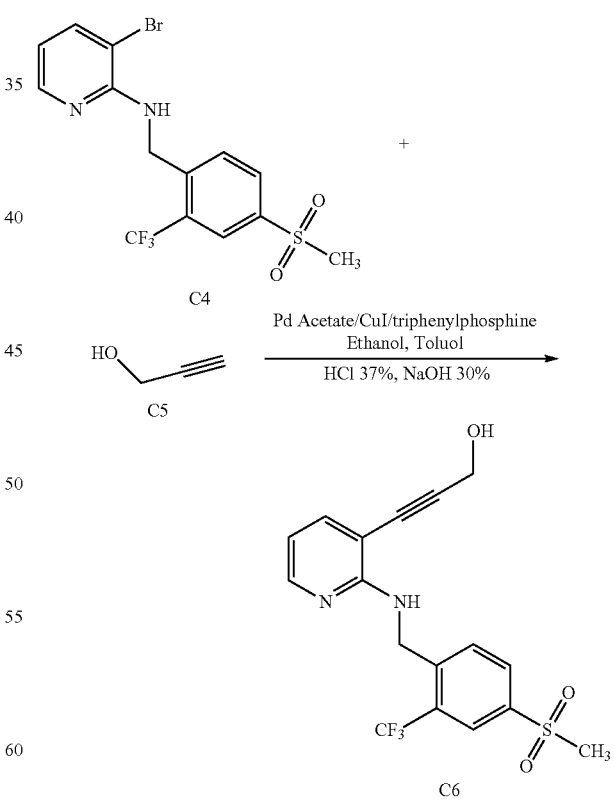

In a 15 L double jacketed vessel, 1.8 Kg of C4 (3-Bromo-N-{[4-methanesulfonyl-2-(trifluoromethyl)phenyl]methyl}pyridin-2-amine), 0.91 kg of potassium carbonate and 0.17 kg of triphenylphosphine were suspended in 6.5 kg of toluol. In alternative embodiments toluene can be substituted for toluol. 0.31 kg of propargyl alcohol (C5) and 0.3 kg of ethanol were added. After an efficient inertisation with nitrogen (three fold depressurizing below 100 mbar followed by re-pressurizing with nitrogen to 1 bar), palladium acetate (4.9 g) and copper iodide (41.9 g) were added as a slurry in ethanol (0.7 kg). After an additional inertisation with nitrogen (same conditions described above), the temperature was increased to 75° C. The mixture was constantly stirred until the conversion was above 98% (checked by an in-process control by HPLC). Aging is a function of the catalyst activity and loading. In this instance, about 10-14 h was required with 1 mol % palladium acetate. Afterwards, solids were removed by filtration and the vessel and nutsche were rinsed with a mixture of toluene and ethanol 9:1 by weight (total weight 2.5 kg). The clear filtrate was charged to a second vessel, diluted with water (12.6 kg) and ethanol (0.8 kg) and made acidic with concentrated hydrochloric acid (0.6 kg). After 30 minutes stirring at 50° C., the phases were split. The lower aqueous phase (containing C6 hydrochloride) was transferred in a tank, while the remaining organic phase was extracted a second time with a mixture of ethanolic hydrochloric acid (1.8 kg water, 0.3 kg ethanol and 90 g HCl 37%). After removal of the organic phase and cleaning of the vessel with ethanol, the aqueous phases were charged again via a polishing filter and diluted with more ethanol (6.4 kg). The pH was made alkaline by adding caustic soda (0.9 kg) while keeping the temperature between 50-60° C. Then after seeding with C6 (30 g as a slurry in ethanol/water 3:7), the solution was aged for 2 h and cooled to 0° C. within 4 h. The resulting product was isolated by filtration. The moist cake was washed with ethanol/water 3:7 (3 kg) and water (6 kg) and dried under vacuum (60° C., <10 mbar) to yield C6 as an off-white solid. The approximate yield was 1.7 kg. The estimated yield percentage was about 90% and the purity was greater than 99%.

Example 3a

Preparation of Compound A

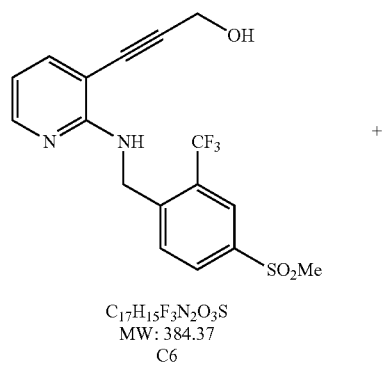

Compound A $C_{17}H_{15}F_3N_2O_3S$
MW: 384.37
C6

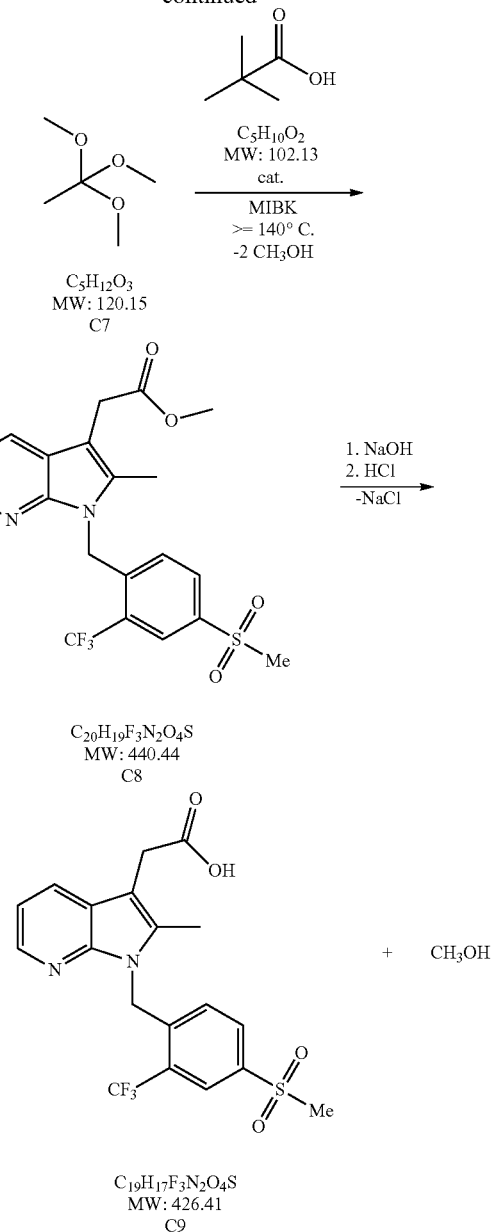

Production of C8: Compound C6, (3-[2-({[4-Methanesulfonyl-2-(trifluoromethyl)-phenyl]methyl}amino)pyridin-3-yl]prop-2-yn-1-ol) (1000 g, 2600 mmol) was dissolved in a mixture of methyl isobutyl ketone (MIBK, 1000 ml), 625 g (5200 mmol) of C7 (trimethoxy-orthoacetate), and pivalic acid (213 g, 50% in methyl isobutyl ketone). The mixture was heated within 2 h to 140° C. under a $N_2$ over-pressure of 1-4 bar. During the reaction methanol was formed and removed from the vessel by a pressure-regulated valve. After 4 h a second portion of methyl isobutyl ketone, C7 (313 g, 2605 mmol) and pivalic acid (106 g, 50% in methyl isobutyl ketone) was added and the mixture was heated for 6 h at 145° C. under a $N_2$ over-pressure of 1.1-1.3 bar. The resultant product was a solution of C8 (Methyl 2-(1-{[4-methanesulfonyl-2-(trifluoromethyl)phenyl]methyl}-2-methyl-1H-pyrrolo[2,3-b]pyridin-3-yl)acetate). Conversion rate was measured at 99% and yield was 84%.

Conversion to Compound A:

The resulting solution was concentrated under vacuum at 100° C./200 mbar and water (6000 ml). A sodium hydroxide solution (1734 g, 30%, 13 mol) was added to the mixture and heated for 4 h at 50° C. The solution was distilled again at 100° C./100 mbar. The phases were separated at 50° C. and the water phase was extracted with methyl isobutyl ketone (2000 ml). Again the phases were separated and the water phase was filtered at 50° C. To the filtrate methyl isobutyl ketone (5000 ml) was added and the aqueous solution neutralized in 2 portions with hydrochloric acid (963 g, 37%, 9.8 mol) to pH 4-4.5. The phases were heated to 80° C. and the organic phases separated. Water (1000 ml) was added to wash the organic phase and after phase separation the organic phase was cooled down to 70° C. Seed crystals of Compound A were added along with heptane (1000 ml). The resulting suspension was stirred for 30 minutes before cooling further down to 0° C. within 3 h. The suspension was stirred for 3 h at 0° C. and then filtered through a nutsche. The filter cake was washed first with pre-cooled HPTF/methyl isobutyl ketone (1000 g, 5:1), then with acetone/water (1000 g, 1:2) and finally with water (1000 g). Wet Compound A was dried in the oven at 60° C. for 8 h under vacuum to isolate 804 g of compound A. The conversion was calculated to be 99%; the yield was 79%.

Example 3b

Preparation of Compound A

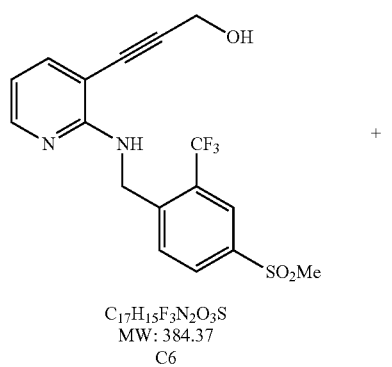

$C_{17}H_{15}F_3N_2O_3S$
MW: 384.37
C6

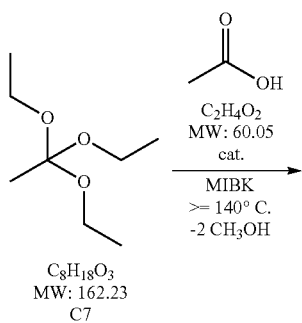

$C_8H_{18}O_3$
MW: 162.23
C7

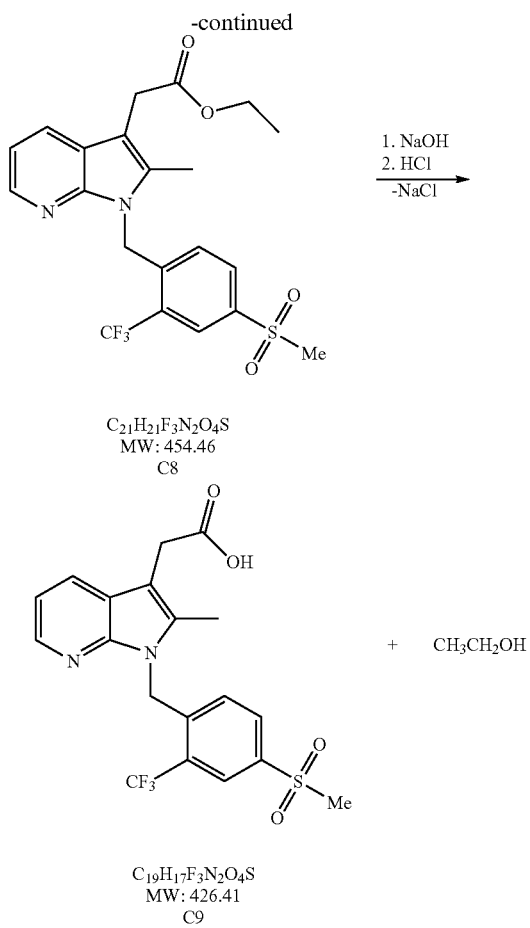

Production of C8:

Compound C6, (3-[2-({[4-Methanesulfonyl-2-(trifluoromethyl)-phenyl]methyl}amino)pyridin-3-yl]prop-2-yn-1-ol) (20 g, 52 mmol) was dissolved in a mixture of methyl isobutyl ketone (MIBK, 125 g), 25.3 g (156 mmol) of 1,1,1-triethoxyethane, and acetic acid (0.625 g, 10 mmol). The mixture was heated within 40 minutes to 140° C. under a $N_2$ over-pressure of 1-4 bar. During the reaction ethanol was formed and removed from the vessel by a pressure-regulated valve. After 3.5 h a second portion of acetic acid (0.625 g) was added and the mixture was heated for 3.5 h at 140° C. under a $N_2$ over-pressure of 1-4 bar. The resultant product was a solution of Ethyl 2-(1-{[4-methanesulfonyl-2-(trifluoromethyl)phenyl]methyl}-2-methyl-1H-pyrrolo[2,3-b]pyridin-3-yl)acetate and the conversion rate was measured at 98% and the yield 90%. The solution was filtered and 40 g MIBK was added. The solution was heated to IT=80° C. and cooled down within 3 h to IT=20° C. At an IT of 65° C. seed crystals were added. At IT 20° C. intermediate C8 was isolated and washed with 40 g MIBK and dried in the oven at IT=60° C./20 mbar.

Conversion to Compound A:

The intermediate C8 was concentrated under vacuum at 100° C./200 mbar and water (6000 ml). A sodium hydroxide solution (1734 g, 30%, 13 mol) was added to the mixture and heated for 4 h at 50° C. The solution was distilled again at 100° C./100 mbar. The phases were separated at 50° C. and the water phase was extracted with methyl isobutyl ketone (2000 ml). Again the phases were separated and the water phase was filtered at 50° C. To the filtrate methyl isobutyl ketone (5000 ml) was added and the aqueous solution neutralized in 2 portions with hydrochloric acid (963 g, 37%, 9.8 mol) to pH 4-4.5. The phases were heated to 80° C. and the organic phases separated. Water (1000 ml) was added to wash the organic phase and after phase separation the organic phase was cooled down to 70° C. Seed crystals of Compound A were added along with heptane (1000 ml). The resulting suspension was stirred for 30 minutes before cooling further down to 0° C. within 3 h. The suspension was stirred for 3 h at 0° C. and then filtered through a nutsche. The filter cake was washed first with pre-cooled HPTF/methyl isobutyl ketone (1000 g, 5:1), then with acetone/water (1000 g, 1:2) and finally with water (1000 g). Wet Compound A was dried in the oven at 60° C. for 8 h under vacuum to isolate 804 g of compound A. The conversion was calculated to be 99%; the yield was 79%.

Example 3c

Alternative Preparation of Compound A

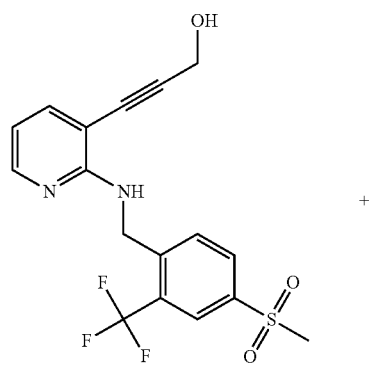

Exact Mass: 384.08

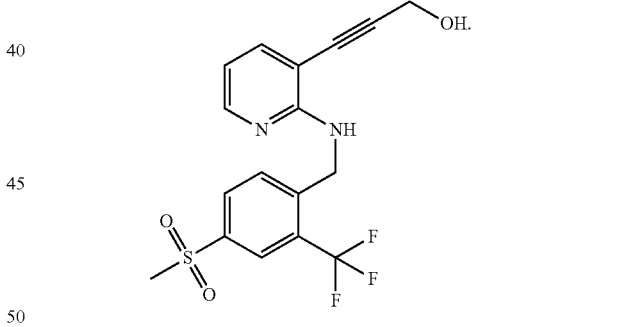

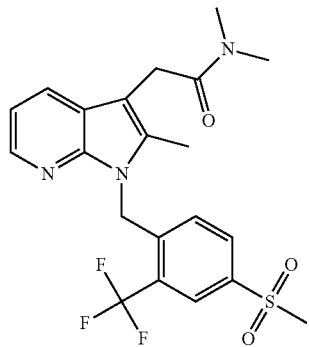

Molecular Weight: 453.48

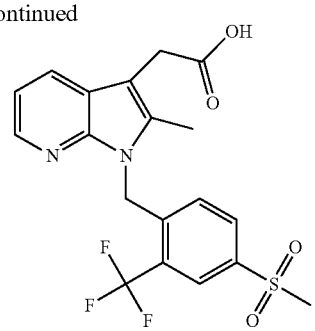

Molecular Weight: 426.41

5 g of (3-[2-({[4-Methanesulfonyl-2-(trifluoromethyl)-phenyl]methyl}amino)pyridin-3-yl]prop-2-yn-1-ol), methyl isobutyl ketone (MIBK, 50 ml), and 1,1-dimethoxy-N,N-dimethylethanamine were put together in a 200 ml reactor and stirred for 15 h at 100° C. The mixture was acidified by addition of hydrochloric acid (15 ml) and kept stirring for 15 h at 100° C. Then water (25 ml) was added, and the temperature was decreased to 50° C. Caustic soda (about 15 ml) was added to set the pH around 12. Then, after phase split and a second extraction with water (10 ml), the combined aqueous phases were diluted with methyl isobutyl ketone (25 ml) and acidified at 80° C. to pH 4 with hydrochloric acid. The mixture was cooled to 70° C., seeded and cooled to 0° C. within 2 h. After 2 h aging at 0° C., the crystalline solid was collected by filtration, washed with methyl isobutyl ketone (10 ml) and water (10 ml), and dried under vacuum at 60° C. until constant weight. Yield 2.93 g.

What is claimed is:

1. The compound of formula

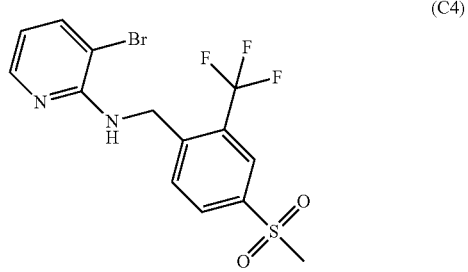 [SMILES: CS(=O)(=O)c1ccc(CNc2ncccc2Br)c(C(F)(F)F)c1]

(C6)

2. A process for preparing the compound of claim 1 comprising (a) reacting a compound of the formula (C4)

with a compound of the formula

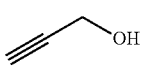
(C5)

in the presence of a catalyst, a reducing agent and 1 or more solvents.

3. The process of claim 2, wherein the catalyst is selected from the group consisting of palladium on charcoal, palladium chloride, palladium acetate, cupric iodide and organic catalysts.

4. The process of claim 2, wherein the solvents are selected from the group consisting of ethanol, toluene, toluol, isopropyl acetate, and mixtures thereof.

5. The process of claim 2, further comprising (b) adding a strong acid to the mixture of C4, C5 and the catalyst.

6. The process of claim 2, further comprising (c) adding a strong base to the mixture of C4, C6 and the catalyst.

7. The process of claim 2 wherein the reducing agent is triphenylphosphine.

8. A process for preparing a compound of formula

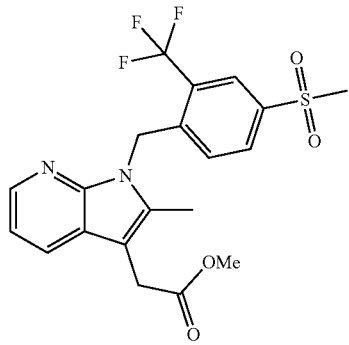
(C8)

comprising reacting a compound of the formula

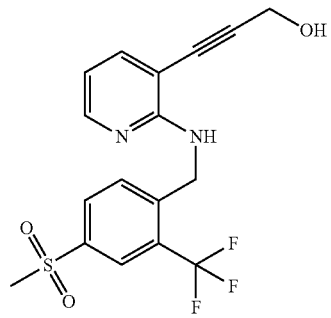
(C6)

with a compound of the formula

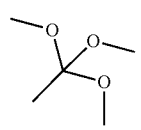
(C7)

in the presence of a catalyst and a solvent.

9. The process of claim 8 wherein the catalyst is an organic acid.

10. The process of claim 9 wherein the organic acid is pivalic acid.

11. The process of claim 8 wherein the solvent is methyl isobutyl ketone.

12. A process for preparing a compound of the formula

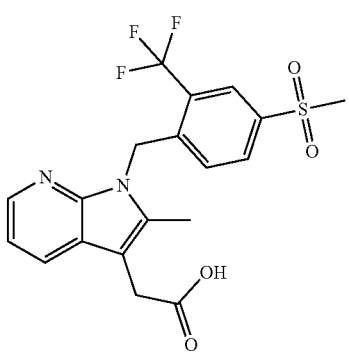
(Compound A)

[1-(4-Methanesulfonyl-2-trifluoromethyl-benzyl)-2-methyl-1H-pyrrolo[2,3-b]pyridin-3-yl]-acetic acid comprising:

(a) reacting a compound of the formula:

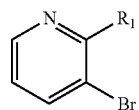
(C1)

wherein R1 is selected from the group consisting of Br or NH2 with a compound of the formula:

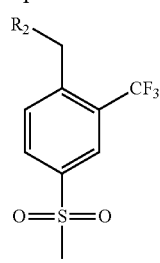
(C2)

wherein R2 is selected from the group consisting of an aldehyde or amine, in the presence of an acid, to form a compound of the formula

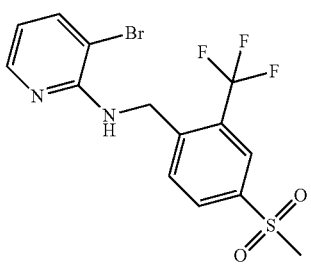
(C4)

(b) reacting the compound of formula C4 with a compound of the formula

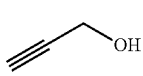
(C5)

in the presence of a catalyst, a reducing agent and 1 or more solvents to form a compound of the formula

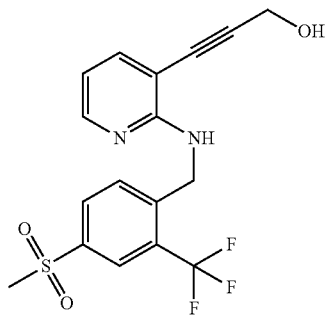
(C6)

(c) reacting the compound of formula C6 with a compound of the formula

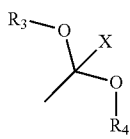
(C7)

wherein R3 and R4 are each independently a $C_1$-$C_6$ alkyl group which may be the same or different, and X is Y—Z, where Y is N, S, $SO_2$, or O and Z is H, O or a $C_1$-$C_6$ alkyl to form a compound of formula

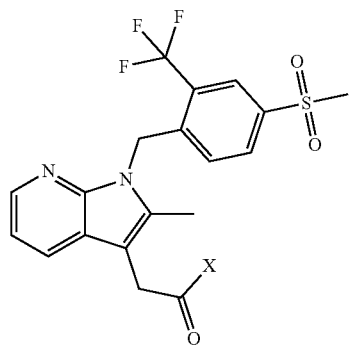

or reacting a compound of formula C6 with a compound of the formula (C7)

in the presence of a catalyst and a solvent to form a compound of the formula (C8)

(d) Converting the compound of formula C8 to Compound A by saponification of C8 in the presence of a strong base.

13. The process of claim 12 wherein the acid in step (a) is selected from the group consisting of 1-p-toluenesoulfonic acid, trifluoroacetic acid, trichloroacetic acid and oxalic acid.

14. The process of claim 12, wherein the catalyst in step (b) is selected from the group consisting of palladium on charcoal, palladium chloride, palladium acetate, cupric iodide and organic catalysts.

15. The process of claim 12, wherein the solvents in step (b) are selected from the group consisting of ethanol, toluene, toluol, isopropyl acetate, and mixtures thereof.

16. The process of claim 12, wherein step (b) further comprises adding a strong acid to the mixture of C4, C5 and the catalyst.

17. The process of claim 12, wherein step (b) further comprises adding a strong base to the mixture of C4, C6 and the catalyst.

18. The process of claim 12 wherein the reducing agent in step (c) is triphenylphosphine.

19. The process of claim 12 wherein the catalyst in step (c) is an organic acid.

20. The process of claim 19 wherein the organic acid is pivalic acid.

* * * * *